(12) United States Patent
Sussman et al.

(10) Patent No.: US 8,852,091 B2
(45) Date of Patent: Oct. 7, 2014

(54) DEVICES, SYSTEMS, AND METHODS FOR PUPIL EXPANSION

(75) Inventors: Glenn R. Sussman, Laguna Niguel, CA (US); Steven T. Charles, Memphis, TN (US); Hsin S. Chin, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 161 days.

(21) Appl. No.: 13/438,881

(22) Filed: Apr. 4, 2012

(65) Prior Publication Data
US 2013/0267988 A1   Oct. 10, 2013

(51) Int. Cl.
*A61B 17/02* (2006.01)

(52) U.S. Cl.
USPC .................. 600/236; 606/107; 600/208

(58) Field of Classification Search
USPC .................................. 600/201–246
See application file for complete search history.

(56) References Cited

U.S. PATENT DOCUMENTS

| | | | |
|---|---|---|---|
| 645,530 A | 3/1900 | Marston | |
| 2,634,726 A | 4/1953 | Hanson | |
| 2,697,438 A | 12/1954 | Hickey | |
| 2,748,769 A | 6/1956 | Huber | |
| 3,589,363 A | 6/1971 | Banko et al. | |
| 3,659,607 A | 5/1972 | Banko | |
| 3,693,613 A | 9/1972 | Kelman | |
| 3,805,787 A | 4/1974 | Banko | |
| 3,882,855 A * | 5/1975 | Schulte et al. | 600/206 |
| 4,014,333 A | 3/1977 | McIntyre | |
| 4,180,074 A | 12/1979 | Murry et al. | |
| 4,223,676 A | 9/1980 | Wuchinich et al. | |
| 4,257,406 A | 3/1981 | Schenk | |
| 4,387,706 A * | 6/1983 | Glass | 600/208 |
| 4,493,694 A | 1/1985 | Wuchinich | |
| 4,515,583 A | 5/1985 | Sorich | |
| 4,573,979 A | 3/1986 | Blake | |
| 4,578,059 A | 3/1986 | Fabricant et al. | |
| 4,609,368 A | 9/1986 | Dotson, Jr. | |
| 4,610,674 A | 9/1986 | Suzuki et al. | |
| 4,634,420 A | 1/1987 | Spinosa et al. | |
| 4,643,717 A | 2/1987 | Cook et al. | |
| 4,652,255 A | 3/1987 | Martinez | |
| 4,681,561 A | 7/1987 | Hood et al. | |
| 4,689,040 A | 8/1987 | Thompson | |
| 4,702,733 A | 10/1987 | Wright et al. | |

(Continued)

FOREIGN PATENT DOCUMENTS

| | | |
|---|---|---|
| CA | 2214566 C | 8/2001 |
| DE | 9320127 U1 | 4/1994 |

(Continued)

OTHER PUBLICATIONS

International Searching Authority, International Search Report, PCT/US2013/030467, Jun. 3, 2013, 7 pages.

(Continued)

*Primary Examiner* — Jerry Cumberledge
(74) *Attorney, Agent, or Firm* — Kenneth D. Bassinger

(57) ABSTRACT

A pupil expander is disclosed. The pupil expander comprises a support member sized to expand a pupil and a plurality of engaging portions. The plurality of engaging portions are coupled to and spaced about the support member. The engaging portions have a recess and are shaped and sized to receive an inner margin of an iris.

19 Claims, 9 Drawing Sheets

(56) References Cited

U.S. PATENT DOCUMENTS

| | | | |
|---|---|---|---|
| 4,705,500 A | 11/1987 | Reimels et al. | |
| 4,713,051 A | 12/1987 | Steppe et al. | |
| 4,737,153 A | 4/1988 | Schimamura et al. | |
| 4,782,820 A * | 11/1988 | Woods | 600/208 |
| 4,787,889 A | 11/1988 | Steppe et al. | |
| 4,808,154 A | 2/1989 | Freeman | |
| 4,808,170 A | 2/1989 | Thornton et al. | |
| 4,816,017 A | 3/1989 | Hood et al. | |
| 4,816,018 A | 3/1989 | Parisi | |
| 4,832,685 A | 5/1989 | Haines | |
| 4,846,172 A | 7/1989 | Berlin | |
| 4,867,141 A | 9/1989 | Nakada et al. | |
| 4,867,747 A | 9/1989 | Yarger | |
| 4,869,715 A | 9/1989 | Sherburne | |
| 4,897,079 A | 1/1990 | Zaleski et al. | |
| 4,904,238 A | 2/1990 | Williams | |
| 4,921,476 A | 5/1990 | Wuchinich | |
| 4,922,902 A | 5/1990 | Wuchinich et al. | |
| 4,935,005 A | 6/1990 | Haines | |
| 4,973,319 A | 11/1990 | Melsky | |
| 4,973,321 A | 11/1990 | Michelson | |
| 4,980,231 A | 12/1990 | Baker et al. | |
| 4,983,160 A | 1/1991 | Steppe et al. | |
| 4,988,334 A | 1/1991 | Hornlein et al. | |
| 4,989,583 A | 2/1991 | Hood | |
| 4,991,567 A | 2/1991 | McCuen, II et al. | |
| 5,026,393 A | 6/1991 | Mackool | |
| 5,030,210 A | 7/1991 | Alchas | |
| 5,038,756 A | 8/1991 | Kepley | |
| 5,084,009 A | 1/1992 | Mackool | |
| 5,112,339 A | 5/1992 | Zelman | |
| 5,123,903 A | 6/1992 | Quaid et al. | |
| 5,133,159 A | 7/1992 | Nelson | |
| 5,151,084 A | 9/1992 | Khek | |
| 5,154,696 A | 10/1992 | Shearing | |
| 5,163,419 A | 11/1992 | Goldman | |
| 5,163,433 A | 11/1992 | Kagawa et al. | |
| 5,174,279 A * | 12/1992 | Cobo et al. | 600/206 |
| 5,188,589 A | 2/1993 | Wypych et al. | |
| 5,199,943 A | 4/1993 | Wypych | |
| 5,209,719 A | 5/1993 | Baruch et al. | |
| 5,211,625 A | 5/1993 | Sakurai et al. | |
| 5,193,159 A | 7/1993 | Nelson | |
| 5,242,385 A | 9/1993 | Strukel | |
| 5,248,297 A | 9/1993 | Takase | |
| 5,255,669 A | 10/1993 | Kubota et al. | |
| 5,267,533 A | 12/1993 | Smith | |
| 5,282,786 A | 2/1994 | Ureche | |
| 5,284,476 A | 2/1994 | Koch | |
| 5,286,256 A | 2/1994 | Mackool | |
| 5,299,564 A * | 4/1994 | Sabatino | 600/236 |
| 5,318,011 A * | 6/1994 | Federman et al. | 600/236 |
| 5,322,054 A | 6/1994 | Graether | |
| 5,346,502 A | 9/1994 | Estabrook et al. | |
| 5,354,265 A | 10/1994 | Mackool | |
| 5,374,272 A * | 12/1994 | Arpa et al. | 606/107 |
| 5,397,293 A | 3/1995 | Alliger et al. | |
| 5,413,556 A | 5/1995 | Whittingham | |
| 5,427,088 A | 6/1995 | Graether | |
| 5,441,045 A * | 8/1995 | Federman et al. | 600/236 |
| 5,472,418 A | 12/1995 | Palestrant | |
| 5,478,338 A | 12/1995 | Reynard | |
| 5,486,162 A | 1/1996 | Brumbach | |
| 5,505,693 A | 4/1996 | Mackool | |
| 5,562,609 A | 10/1996 | Brumbach | |
| 5,593,394 A | 1/1997 | Kanesaka et al. | |
| 5,607,446 A | 3/1997 | Beehler et al. | |
| 5,634,884 A * | 6/1997 | Graether | 600/236 |
| 5,634,912 A | 6/1997 | Injev | |
| 5,645,530 A | 7/1997 | Boukhny et al. | |
| 5,651,783 A | 7/1997 | Reynard | |
| 5,667,489 A | 9/1997 | Kraff et al. | |
| 5,716,328 A | 2/1998 | Grieshaber et al. | |
| 5,725,495 A | 3/1998 | Strukel et al. | |
| 5,730,752 A | 3/1998 | Alden et al. | |
| 5,741,226 A | 4/1998 | Strukel et al. | |
| 5,743,871 A | 4/1998 | Strukel et al. | |
| 5,807,310 A | 9/1998 | Hood | |
| 5,830,192 A | 11/1998 | Van Voorhis | |
| 5,873,851 A | 2/1999 | Nilsson | |
| 5,879,356 A | 3/1999 | Geuder | |
| 5,919,157 A | 7/1999 | Strukel | |
| 5,941,887 A | 8/1999 | Steen et al. | |
| 5,984,904 A | 11/1999 | Steen et al. | |
| 6,013,046 A | 1/2000 | Maaskamp et al. | |
| 6,033,376 A | 3/2000 | Rockley | |
| 6,056,735 A | 5/2000 | Okada et al. | |
| 6,068,643 A * | 5/2000 | Milverton | 606/191 |
| 6,117,151 A | 9/2000 | Urich et al. | |
| 6,132,436 A | 10/2000 | Portney | |
| 6,132,448 A | 10/2000 | Perez et al. | |
| 6,159,175 A | 12/2000 | Strukel et al. | |
| 6,183,480 B1 | 2/2001 | Mackool | |
| 6,224,565 B1 | 5/2001 | Cimino | |
| 6,280,449 B1 | 8/2001 | Blake | |
| 6,299,591 B1 | 10/2001 | Banko | |
| 6,361,520 B1 | 3/2002 | Rockley | |
| 6,398,754 B1 | 6/2002 | Sutton et al. | |
| 6,428,501 B1 | 8/2002 | Reynard | |
| 6,514,515 B1 | 2/2003 | Williams | |
| 6,520,929 B2 | 2/2003 | Zaleski | |
| 6,602,193 B2 | 8/2003 | Chon | |
| 6,605,054 B2 | 8/2003 | Rockley | |
| 6,613,056 B1 | 9/2003 | Brumbach et al. | |
| 6,620,098 B1 * | 9/2003 | Milverton | 600/236 |
| 6,638,289 B1 | 10/2003 | Johnson et al. | |
| 6,648,819 B2 * | 11/2003 | Lee | 600/236 |
| 6,663,614 B1 | 12/2003 | Carter | |
| 6,921,385 B2 | 7/2005 | Clements et al. | |
| 6,966,913 B2 | 11/2005 | Israel | |
| 7,014,629 B2 | 3/2006 | Mackool | |
| 7,063,680 B2 | 6/2006 | Lee et al. | |
| 7,066,923 B2 | 6/2006 | Tjia | |
| 7,094,229 B2 | 8/2006 | Boukhny et al. | |
| 7,276,060 B2 | 10/2007 | Madden | |
| 7,413,542 B2 | 8/2008 | Kucklick et al. | |
| 7,435,214 B2 | 10/2008 | Kucklick et al. | |
| 7,445,596 B2 | 11/2008 | Kucklick et al. | |
| 7,500,947 B2 | 3/2009 | Kucklick et al. | |
| 7,588,553 B2 | 9/2009 | Dewey | |
| 7,601,136 B2 | 10/2009 | Akahoshi | |
| 7,648,713 B2 | 1/2010 | Sawhney | |
| 7,704,244 B2 | 4/2010 | Boukhny et al. | |
| 7,867,190 B2 | 1/2011 | Ponsi | |
| 7,967,775 B2 | 6/2011 | Hong | |
| 7,998,061 B2 | 8/2011 | Kucklick et al. | |
| 8,012,083 B2 | 9/2011 | Kucklick et al. | |
| 8,118,731 B2 | 2/2012 | Kucklick et al. | |
| 8,267,891 B2 | 9/2012 | Dimalanta et al. | |
| 8,359,723 B2 | 1/2013 | Voss | |
| 2001/0034504 A1 | 10/2001 | Zaleski | |
| 2002/0091306 A1 * | 7/2002 | Juan et al. | 600/235 |
| 2002/0091351 A1 | 7/2002 | Rockley | |
| 2002/0165492 A1 | 11/2002 | Davey et al. | |
| 2005/0245886 A1 | 11/2005 | Devine et al. | |
| 2005/0283122 A1 | 12/2005 | Nordgren | |
| 2007/0078470 A1 | 4/2007 | Tjia et al. | |
| 2007/0106300 A1 | 5/2007 | Auld et al. | |
| 2007/0260173 A1 | 11/2007 | Boukhny et al. | |
| 2008/0243139 A1 * | 10/2008 | Dusek | 606/107 |
| 2008/0269888 A1 * | 10/2008 | Malyugin | 623/6.42 |
| 2008/0300531 A1 | 12/2008 | Gills, Jr. | |
| 2008/0319378 A1 | 12/2008 | Ponsi | |
| 2009/0030311 A1 | 1/2009 | Stulen et al. | |
| 2009/0043165 A1 | 2/2009 | Kucklick et al. | |
| 2009/0062607 A1 | 3/2009 | Kucklick et al. | |
| 2009/0093750 A1 | 4/2009 | Herman | |
| 2009/0143806 A1 | 6/2009 | Witt et al. | |
| 2011/0092888 A1 | 4/2011 | Gerg | |
| 2011/0319810 A1 | 12/2011 | Ghannoum | |
| 2012/0041265 A1 | 2/2012 | Kucklick et al. | |

(56) References Cited

U.S. PATENT DOCUMENTS

FOREIGN PATENT DOCUMENTS

| EP | 0269870 | | 6/1988 |
|---|---|---|---|
| EP | 0375302 | | 12/1989 |
| EP | 0376562 | | 12/1989 |
| EP | 0352984 | | 4/1994 |
| EP | 0778750 | | 10/2003 |
| EP | 0778750 | B1 | 10/2003 |
| EP | 1568339 | | 8/2005 |
| FR | 2740028 | A1 | 4/1997 |
| JP | 10-71166 | | 3/1998 |
| JP | 2000-33097 | | 2/2000 |
| WO | WO 96/27334 | | 9/1996 |
| WO | WO 98/16155 | | 4/1998 |
| WO | 99/44514 | A1 | 9/1999 |
| WO | 99/55260 | A1 | 11/1999 |
| WO | WO 99/62411 | | 12/1999 |
| WO | 00/18340 | A1 | 4/2000 |
| WO | 2005/072402 | A2 | 8/2005 |
| WO | 2005/110509 | A1 | 11/2005 |
| WO | WO 2005/110509 | | 11/2005 |
| WO | 2006/105283 | A2 | 10/2006 |
| WO | WO 2006/105283 | | 10/2006 |
| WO | 2006/105283 | A3 | 12/2007 |
| WO | 2008/115455 | A1 | 9/2008 |
| WO | WO 2009/046413 | | 4/2009 |
| WO | WO 2012/082425 | A2 | 6/2012 |

OTHER PUBLICATIONS

International Searching Authority, Written Opinion of the International Searching Authority, PCT/US2013/030467, Jun. 3, 2013, 8 pages.

"Characteristic properties of silicone rubber compounds." Shin-Etsu. Retrived Apr. 29, 2013. Originally published Mar. 2005.

"Silicone rubber." Wikipedia. Retrieved Apr. 29, 2013. Online: <ttp://en.wikipedia.org/wiki/Silicone_rubber>.

"Teflon". Lenntech V.B. Retrieved Apr. 29, 2013. Online: <http://www.lenntech.com/teflon.htm>.

International Preliminary Report on Patentability and the Written Opinion of the International Searching Authority, Issued Jun. 21, 2011 for Application No. PCT/US2009/067860, Filed Dec. 14, 2009; Publication No. WO2010/080356, Published Jul. 15, 2010, 6 pages.

International Searching Authority, International Search Report, PCT/US2011/063242, Apr. 9, 2012, 2 pages.

International Searching Authority, Written Opinion of the International Searching Authority, PCT/US2011/063242, Apr. 9, 2012, 5 pages.

"Scleral and Corneal Burns During Phacoemulsification With Viscoelastic Materials;" ECRI, vol. 17, No. (12); pp. 377-379; Dec. 1988.

Polack, et al; "The Phacoemulsification Procedure, III, Corneal Complications;"Invest. Ophthalmol. Visual Sci; pp. 39-46; Jan. 1977.

Strobel, et al; "Phaco-Emulsification and Planned ECCE: Intraoperative Differences in Intraocular Heating;" EUR J. Implant Ref. Surg., vol. 3; pp. 135-138; Jun. 1991.

Excerpts from www.alconlabs.com/us/aj/products, 1998-2002.

Malyugin, B., "Malyugin Ring for Small Pupil Phaco Cases", Cataract & Refr. Surg. Today, Mar. 2008, 4 pgs.

Boughton, B., "New Pupil Expansion Ring for Floppy Iris", Amer. Academy of Ophthomol—EyeNet Online Magazine, 2008, 3 pgs, original URL: http://aao.org/publications/eyenet/200801/cataract.cfm.

Skorin Jr., Leonid, "How to Avoid Intraoperative Floppy Iris Syndrome", Review of Ophthomol. Nov. 2010, 5 pgs.

Malyugin, B., "Small Pupil Phaco Surgery: A New Technique", Ann. Ophthomol., 2007, 39:3, pp. 185-193.

\* cited by examiner

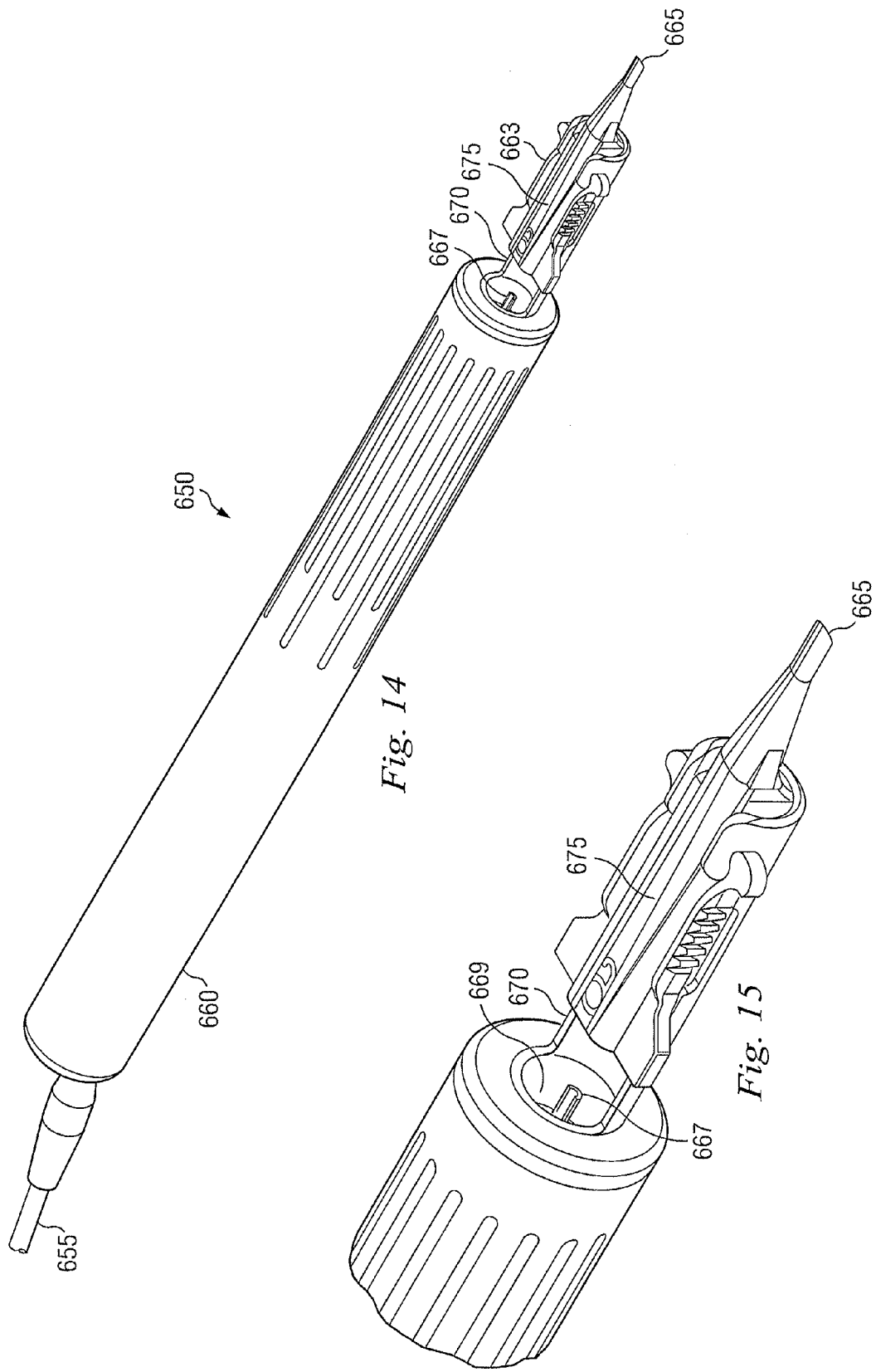

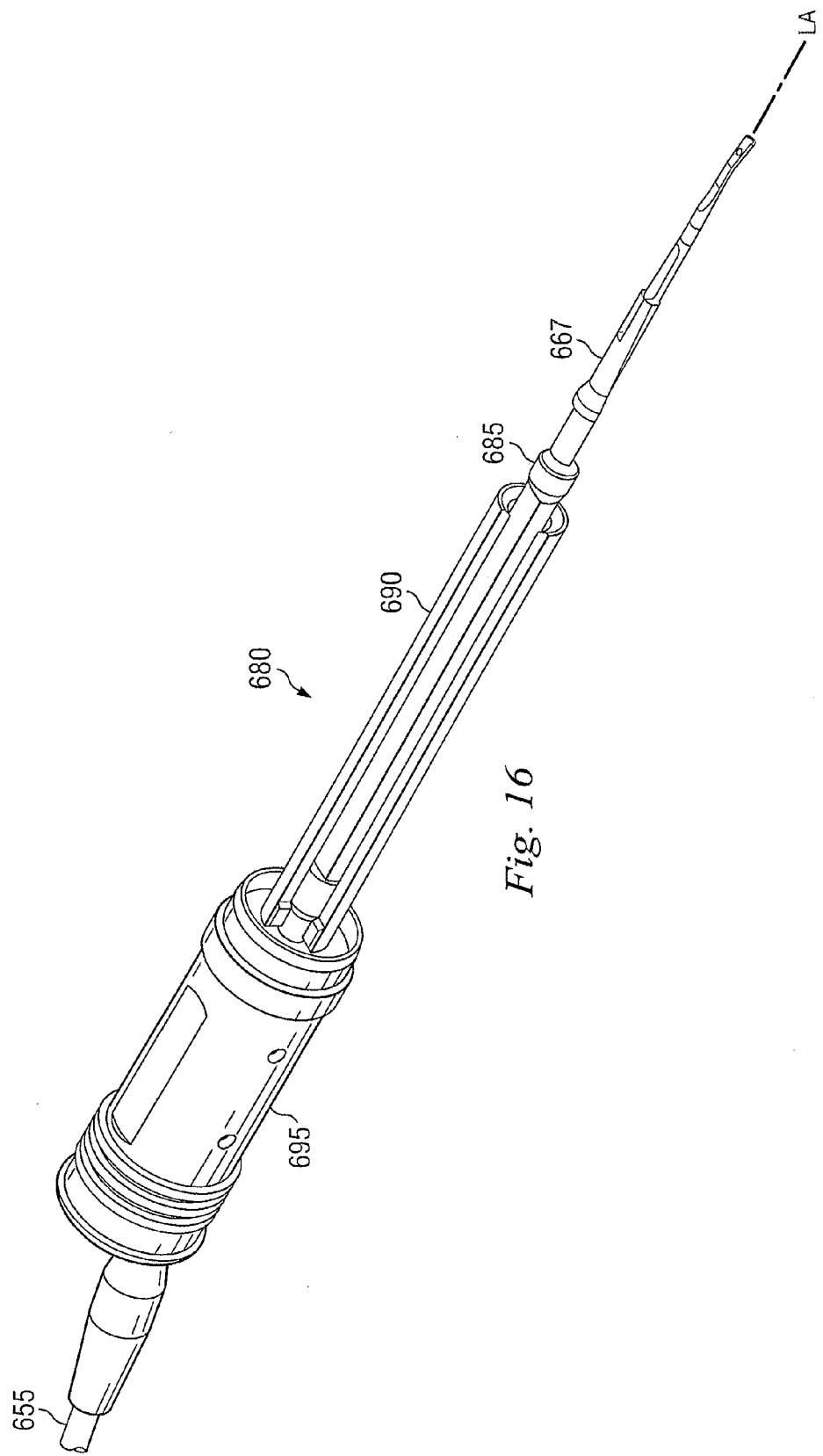

DEVICES, SYSTEMS, AND METHODS FOR PUPIL EXPANSION

FIELD OF THE INVENTION

The present disclosure is directed to devices, systems and methods for use in an ophthalmic procedure, and more particularly, to devices, systems, and methods for pupil expansion as a part of an ophthalmic surgery.

BACKGROUND

Several ophthalmic surgeries and procedures require dilation of the pupil to enable adequate viewing of the interior of the eye, and in particular the posterior chamber and posterior segment portions of the eye. For example, adequate dilation of the eye is generally essential during cataract and posterior segment surgery. Pupil dilation may also be required to extract foreign bodies lodged behind the iris.

In some instances, a patient's pupil may resist dilation efforts. For example, past surgery, recent trauma, and exfoliation syndrome may prevent the pupil from dilating adequately.

Various approaches have been taken to obtain and/or enhance pupil dilation. Some approaches are principally pharmacological, while other approaches involve surgery (i.e., ocular incisions) or mechanical manipulation of the iris. Pharmaceutical approaches are generally less preferred because, in a significant number of patients, the pharmaceuticals do not effectively dilate the pupil. Surgical approaches, including sphincterotomies and sector iridectomies, are also generally disfavored because of the possibility of surgical complications and cosmetic consequences. Another surgical approach uses sutures to tack the retracted iris through the scleral wall, but this approach requires delicate surgery and is time consuming. A hybrid surgical-mechanical approach involves the use of intraocular tacks that tack the iris to the sclera in a retracted position, but this approach requires the insertion of a surgical instrument behind the iris without adequate visualization, and may lead to inadvertent puncture of the iris and release of pigment into the eye. A mechanical approach for dilating or expanding the pupil includes pulling back the iris with translimbal iris hooks, which may cause damage to the iris tissue. Moreover, both the intraocular tacks and the iris hooks occasionally shift or slip from place, which can cause substantial complications during an ophthalmic surgery or other procedure.

The devices, systems, and methods disclosed herein overcome one or more of the deficiencies of the prior art.

SUMMARY

The disclosure relates generally to, and encompasses, devices, systems, and methods for use in ophthalmic surgery, and more specifically to ophthalmic devices, systems, and methods for retracting the iris to expand the pupil and maintain the pupil in an expanded state during an ophthalmic surgery or other procedure, thereby facilitating the diagnosis and/or the treatment of various eye conditions.

In one exemplary embodiment, the present disclosure describes a pupil expander comprising a support member and a plurality of engaging portions. The support member is sized to expand a pupil. The engaging portions are coupled to and spaced about the support member. The engaging portions each have a recess shaped and sized to receive an inner margin of an iris.

In some embodiments, the plurality of engaging portions extend radially from the support member.

In some embodiments, the engaging portions each has a contact surface having a curvature substantially corresponding to the curvature of the inner margin of the iris.

In another exemplary embodiment, the present disclosure describes a pupil expander for dilating a pupil and maintaining the pupil in a dilated state during an ophthalmic procedure. The pupil expander comprises a support member and a plurality of engaging portions coupled to the support member. The support member is capable of self-expansion into a predetermined shape configuration sized to dilate the pupil. The engaging portions each include an anterior flange and a posterior flange extending radially from the support member, and a contact surface is formed therebetween that is configured to seat an inner margin of an iris.

In another exemplary embodiment, the present disclosure describes a method for stretching an iris to dilate a pupil in an eye. The method comprises forming an incision in the eye, inserting a pupil expander comprising engaging portions coupled to a support member having an unexpanded condition and an expanded condition into the pupil through the incision while the support member is in an unexpanded condition, and expanding the support member in the pupil until the engaging portions receive an inner margin of the iris and stretch the iris.

In another exemplary embodiment, the present disclosure describes a method for positioning a pupil expander relative to an eye. The method comprises inserting the pupil expander in an unexpanded condition into a lumen of delivery/extraction apparatus sized to receive the pupil expander, wherein the delivery/extraction apparatus comprises a plunger longitudinally disposed within a tubular housing and an actuating mechanism configured to cause longitudinal translation of the plunger along a longitudinal axis of the housing. The method also comprises activating the actuating mechanism to move the plunger along the longitudinal axis of the housing toward a distal end of the delivery/extraction apparatus to displace the pupil expander from the lumen of the delivery/extraction apparatus into the eye.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

FIG. 14 illustrates a perspective view of an exemplary pupil expander injection apparatus according to one embodiment of the present disclosure.

FIG. 15 illustrates an enlarged perspective view of a distal portion of the exemplary pupil expander injection apparatus shown in FIG. 14.

FIG. 16 illustrates a partially cut-away perspective view of an exemplary actuating mechanism of the exemplary pupil expander injection apparatus shown in FIG. 14.

DETAILED DESCRIPTION

Figure 1:
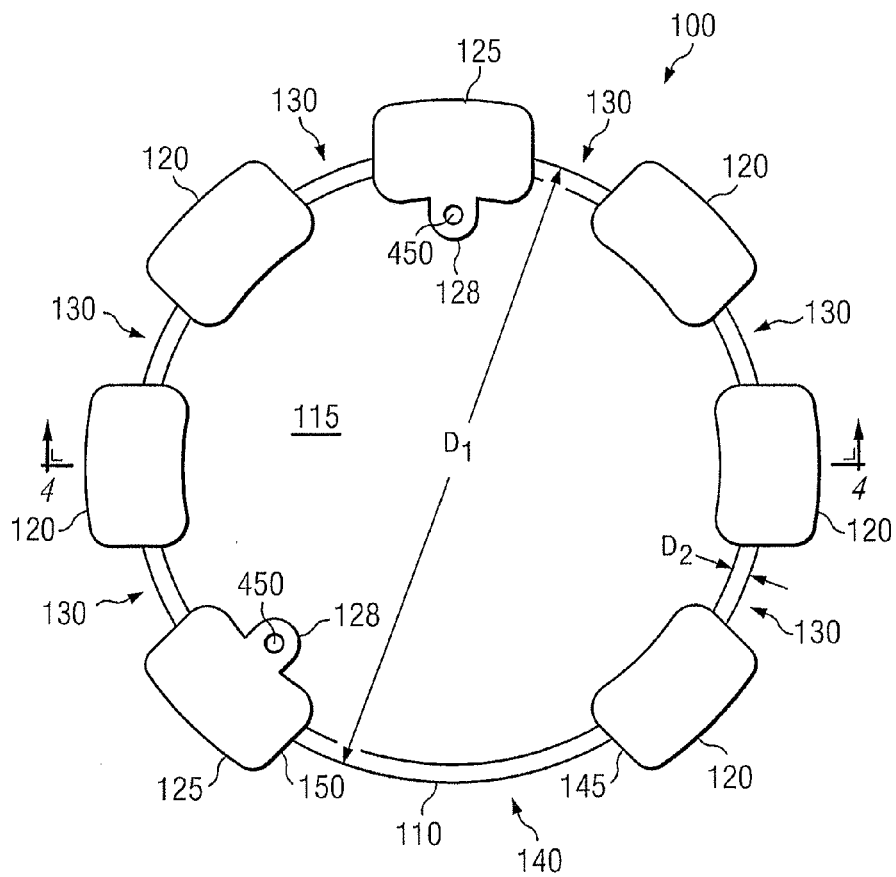
FIG. 1 illustrates a top plan view of an exemplary pupil expander according to one embodiment of the present disclosure.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to ophthalmic pupil expanders and associated delivery systems and methods used in ophthalmic surgeries and procedures requiring adequate visualization of the interior of the eye, such as, by way of non-limiting example cataract surgeries, vitreoretinal surgeries, and other posterior segment surgeries. In some instances, embodiments of the present disclosure may be configured to be part of an ophthalmic surgical system.

The present disclosure provides a pupil expander utilizing a shape memory ring with iris cups to dilate a pupil and maintain the pupil in a dilated condition while maintaining chamber stability during an ophthalmic surgery or procedure. The pupil expander can assume an unexpanded condition to facilitate atraumatic insertion into and removal from an eye through a primary incision, and can assume a predetermined, expanded condition within the eye. In its expanded condition, the pupil expander comprises a substantially circular ring with substantially pliable iris engaging portions referred to here as iris cups that support the pupil expander against an iris, allowing the pupil expander to be self-stabilized and self-retained in the eye throughout the surgery (i.e., without the use of sutures, tacks, or a manually held instrument). Therefore, the pupil expander disclosed herein enhances pupil dilation and maintenance of pupil dilation throughout an ophthalmic surgery or other procedure, thereby facilitating the diagnosis and/or the treatment of various eye conditions. The present disclosure also provides an inserter that may be used to insert and remove the pupil expander.

FIG. 1 illustrates a pupil expander 100 in an expanded condition according to one embodiment of the present disclosure. Though the pupil expander 100 shown in FIG. 1 is configured for use in ophthalmic surgeries, such as vitreoretinal surgery, the pupil expander may be used in any ophthalmological context, including diagnosis, treatment, ex vivo evaluation, and postmortem evaluation. The pupil expander 100, which is capable of self-retention on the eye of a patient throughout a surgical procedure, may enhance visualization of and access to structures within the interior of an eye, such as within the posterior segment during a vitreoretinal procedure. Some embodiments of the pupil expander 100 may be configured as disposable single-use device, thereby allowing the use of a new pupil expander for each patient.

The pupil expander 100 comprises a support member 110 having a central opening 115 and a plurality of iris cups 120, 125 disposed circumferentially on the support member 110. In the pictured embodiment, the pupil expander 100 includes five iris cups 120 and two iris cups 125 fixedly arranged in a symmetrical pattern on the support member 110. The iris cups 120, 125 are spaced apart along the support member 110 to form a plurality of recesses 130 and a recess 140. The iris cups 120, 125 extend radially from the support member 110 such that if the pupil expander 100 is centrally positioned in an expanded condition within the pupil of an eye, the iris cups would contact and extend the iris of the eye.

In other embodiments, the pupil expander may include any number and arrangement of iris cups that allow for adequate pupil dilation and self-stabilization within the eye. The number and arrangement of the iris cups 120, 125 may be selected in consideration of, among other factors, the type of procedure to be performed, the surgeon's preferred surgical technique, or locations at which surgical instruments (e.g., trocar cannulas) are typically placed for ophthalmological surgical procedures (e.g., a surgical procedure involving the posterior segment or posterior chamber of the eye).

The support member 110 is shaped and configured to enable sufficient pupil dilation to allow visualization of or access to interior regions of the eye. The support member 110 is expandable from an unexpanded condition to an expanded condition having a predetermined shape configuration. For example, in the embodiment pictured in FIG. 1, the support member 110, in an expanded condition, comprises a continuous, closed, annular ring with a predetermined circular shape that substantially corresponds to the shape of an average human pupil. In other embodiments, the support member comprises an open ring or a C-shaped ring. In other embodiments, the support member may having any of a variety of predetermined shapes in the expanded condition, including, by way of non-limiting example, an oval, a horseshoe, or an elliptical shape.

The support member 110 is constructed from a structurally deformable biocompatible material that can elastically or plastically deform without compromising its integrity. The support member 110 may be made from a self-expanding biocompatible material, such as Nitinol or a resilient polymer, or an elastically compressed spring temper biocompatible material. Other materials having shape memory characteristics, such as particular metal alloys, may also be used. The shape memory materials allow the support member to be restrained in a low profile configuration during delivery into the eye and to resume and maintain its expanded shape in vivo after the delivery process. The material composition of the support member 110 resiliently biases the support member toward the expanded condition. In particular, in this example, the support member is formed of an elastic material allowing the support member to elastically deform to an unexpanded state to facilitate delivery through small incision (e.g., through a tubular delivery instrument), and spring back to an expanded state as it enters the eye. In other embodiments, the support member may be made of a shape memory alloy having a memory shape in the expanded configuration. The support member 110 may be coated with any of a variety of biocompatible materials, including, by way of non-limiting example, polytetrafluoroethylene (PTFE).

The support member 110 may be sized to have an external diameter D1 ranging from, for example only, approximately 6.0 to 8.0 mm in an expanded condition to provide adequate visualization of or access to the interior of the eye while remaining small enough to limit interference with other surgical instruments and/or a surgeon's hand during an ophthalmological procedure. Other diameter ranges are contemplated. In the pictured embodiment in FIGS. 1 and 2, the support member 110 has a substantially circular cross-section and a cross-sectional diameter D2 ranging from approximately 0.05 to 0.15 mm, although other sizes are contemplated. In other embodiments, the support member 110 may have any of a variety of cross-sectional shapes, including without limitation, rectangular, ovoid, square, rhomboid, and crescent.

As shown in FIG. 1, any one of the recesses 130, 140 are shaped and defined by the support member 110 and a periphery 145 of the iris cups 120 and/or a periphery 150 of the iris cups 125. For example, the recess 140 is shaped and defined by the support member 110, the periphery 145, and the periphery 150. In the pictured embodiment, the iris cups 120, 125 are spaced substantially equally from each other, thereby forming substantially equally sized recesses 130. In other embodiments, the iris cups are unequally spaced from each other, thereby creating unequally sized recesses. The recess 140 is sized wider than the recesses 130 to allow passage of surgical instruments, such as, by way of non-limiting example, a phaco tip. The number and arrangement of the recesses 130, 140 corresponds to the number and arrangement of the iris cups 120, 125. For example, in the pictured embodiment, the pupil expander 100 includes seven total iris cups 120, 125 and seven total recesses 130, 140. Alternate embodiments may include any number and arrangement of recesses 130, 140. Some embodiments may include an open support member having a space or gap instead of the wide recess 140.

For simplicity of description, only one of the iris cups (120) will be described in detail, and it should be understood that the iris cups 120, 125 are substantially identical, except for the differences described herein.

Figure 2:
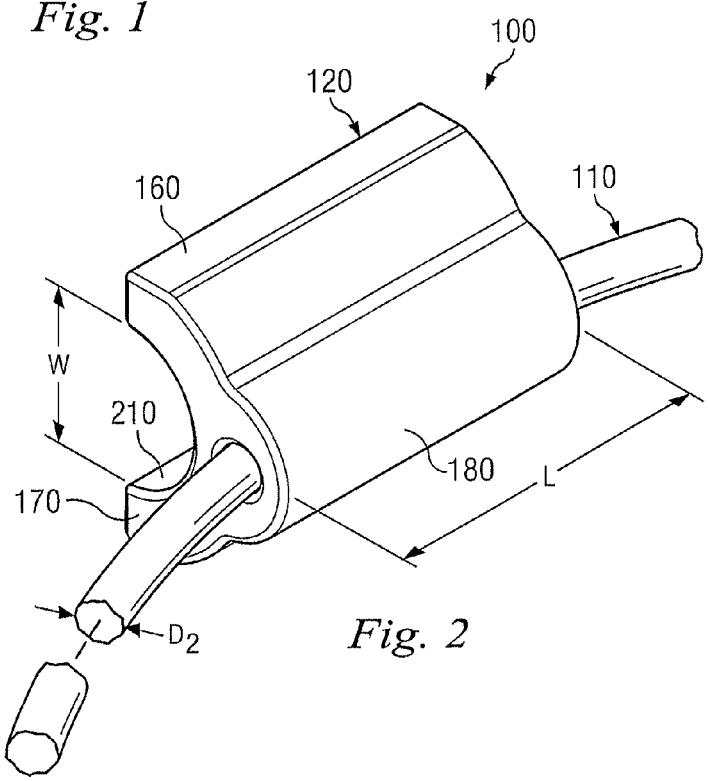
FIG. 2 illustrates a perspective view of a portion of the pupil expander shown in FIG. 1, showing an iris cup according to one embodiment of the present disclosure.
Figure 3:
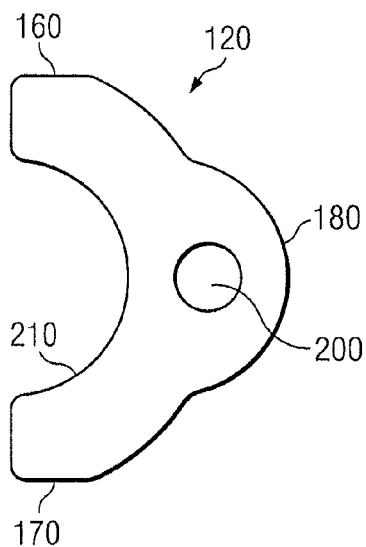
FIG. 3 illustrates a side view of the iris cup shown in FIG. 2.

FIG. 2 illustrates a portion of the pupil expander 100, showing a portion of the support member 110 and one iris cup 120, which is again illustrated in FIG. 3. The iris cup 120 is shaped and configured to surround an internal margin of an iris when the pupil expander 100 is positioned in an average eye. In the pictured embodiment, the iris cup 120 extends radially away from the support member 110 to form the farthest periphery of the pupil expander 100.

As shown in FIGS. 2 and 3, the iris cup 120 includes an anterior flange 160, a posterior flange 170, and a central portion 180. The central portion 180 forms the junction between the iris cup 120 and the support member 110. In the pictured embodiment of FIG. 3, the central portion 180 includes a hollow tube 200 which receives the support member therethrough. In some embodiments, the anterior flange and the posterior flange are configured to conform around the inner margin of the iris.

The anterior flange 160, the posterior flange 170, and the central portion 180 cooperate to form a contact surface 210, which is shaped and configured to contact and engage iris tissue at the internal margin of the iris and seat a portion of the inner margin of the iris. In the pictured embodiment, the contact surface 210 is shaped as a receiving recess formed between the anterior and posterior flanges. The contact surface 210 has a width W extending between the anterior flange 160 and the posterior flange 180. The width W forms the height of the recess. In one embodiment, the width W is within the range of about 0.30 to 0.70 mm, and preferably within the range of about 0.35 to 0.60 mm. The contact surface 210 has a longitudinal length L extending the entire length of the iris cup. In one embodiment, the length L is within the range of about 0.50 to 1.5 mm, and preferably within the range of about 0.65 to 1.0 mm. This length enables the loading on the iris to be distributed over a greater percentage of the iris perimeter, reducing trauma that may occur with point loads. In addition, by using multiple iris cups distributing the loading, the iris is further protected, which may increase the rate of recovery and result in an improved surgical outcome.

In various embodiments, the contact surface 210 may have any of a variety of shapes designed to engage the iris, including without limitation, a C-shape, a more pronounced U-shape, a rectangular shape, a V-shape, and an elliptical shape. In some embodiments, the contact surface has a curvature substantially corresponding to the curvature of the inner margin of the iris. In the pictured embodiment, the contact surface 210 is substantially smooth. In other embodiments, the contact surface may be textured.

In some embodiments, the iris cups are integrally formed with the support member by, for example, injection molding. In other embodiments, the pupil expander comprises a multi-component device with the iris cups attached to the support member at the central portion by any of a variety of attachments mechanisms, including one or more of an adhesive, a threaded engagement, a snap-fit engagement, a frictional engagement, over-molding, heat-shrinking, heat welding, and/or any other mechanism for fixedly connecting the iris cups to the support member.

In some embodiments, the iris cups 120 are formed of a pliable material allowing for some degree of deformation and pliancy. In alternate embodiments, the iris cups are formed of a rigid or semi-rigid material. The iris cups 120 may formed from any of a variety of biocompatible materials, including, by way of non-limiting example, silicone, silicone polyimide, polycarbonate, polymethylmethacrylate (PMMA), nylon, prolene, polyurethane, silastic, polyamide or a combination thereof, or any other biocompatible material having the requisite properties of resilience, flexibility, and suitability for use in ophthalmic procedures. The iris cups 120 may be coated with any of a variety of biocompatible materials, including, by way of non-limiting example, polytetrafluoroethylene (PTFE). In some embodiments, the individual components of the iris cup 120, including anterior flange 160, the posterior flange 170, and the central portion 180, may be formed of different biocompatible materials of varying degrees of pliancy. For example, in some embodiments, the posterior flange may be formed of a more flexible and pliant material than the anterior flange to minimize contact damage or trauma to a lens and a capsule of the eye.

Figure 4:
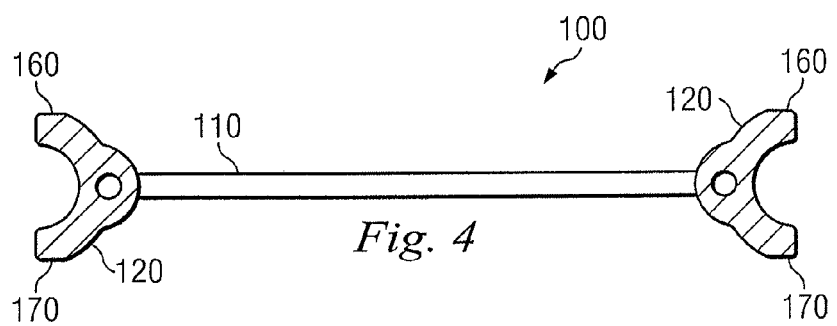
FIG. 4 illustrates a cross-sectional side view of the pupil expander shown in FIG. 1.

FIG. 4 illustrates a cross-sectional side view along the lines 4-4 of the pupil expander 100 shown in FIG. 1. In the pictured embodiment, the iris cups 120 have a symmetrical cross-sectional profile, including anterior flanges 160 and posterior flanges 170 of substantially equal size and cross-sectional shape. Moreover, each iris cup 120 is substantially identical. Thus, the iris cups 120 of the pupil expander are shaped and configured to engage anterior and posterior aspects of the iris to substantially the same extent and in substantially the same manner.

Although the iris cups 120 of the pupil expander 100 are substantially identical in size and cross-sectional shape, other embodiments may include iris cups of varying sizes and shapes.

Figure 5:
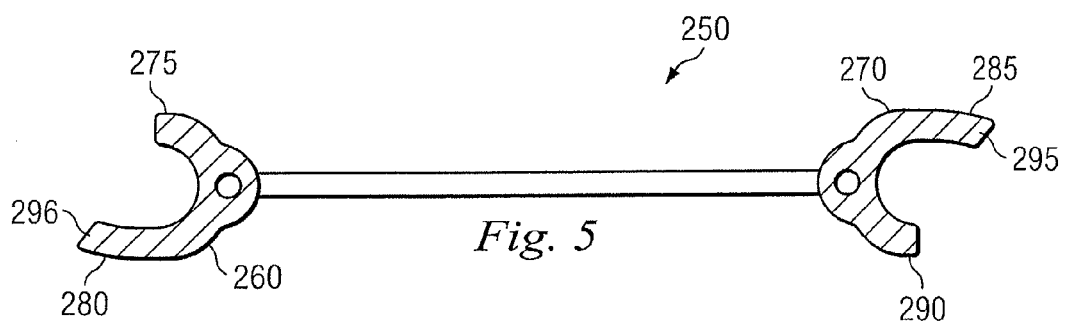
FIG. 5 illustrates a cross-sectional side view of a pupil expander according to another exemplary embodiment of the present disclosure.

For example, FIG. 5 illustrates a cross-sectional side view of a pupil expander 250 according to another embodiment of the present disclosure. The pupil expander 250 includes iris cups of varying cross-sectional profiles. In particular, the pupil expander 250 includes an iris cup 260 and an iris cup 270, which are substantially similar to the iris cups 120 except for the differences described herein. The iris cup 260 includes an anterior flange 275 and a posterior flange 280, and the iris cup 270 includes an anterior flange 285 and a posterior flange 290. As shown in FIG. 5, the iris cups 260, 270 have opposite cross-sectional profiles, wherein the anterior flange 285 of the iris cup 270 and the posterior flange 280 of the iris cup 260 are longer than the posterior flange 290 of the iris cup 270 and the anterior flange 275 of the iris cup 260, respectively. Moreover, the distal ends 295, 296 of the anterior flange 285 of the iris cup 270 and the posterior flange 280 of the iris cup 260, respectively, may be tapered. Thus, the different iris cups 260, 270 of the pupil expander 250 are shaped and configured to engage anterior and posterior aspects of the iris to different extents and in different manners. This combination of varying flanges may tend to center and stabilize the pupil expander within the eye.

Figure 6:
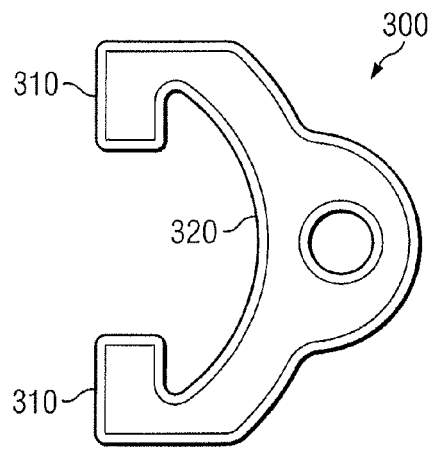
FIG. 6 illustrates a side view of an iris cup according to another exemplary embodiment of the present disclosure.
Figure 7:
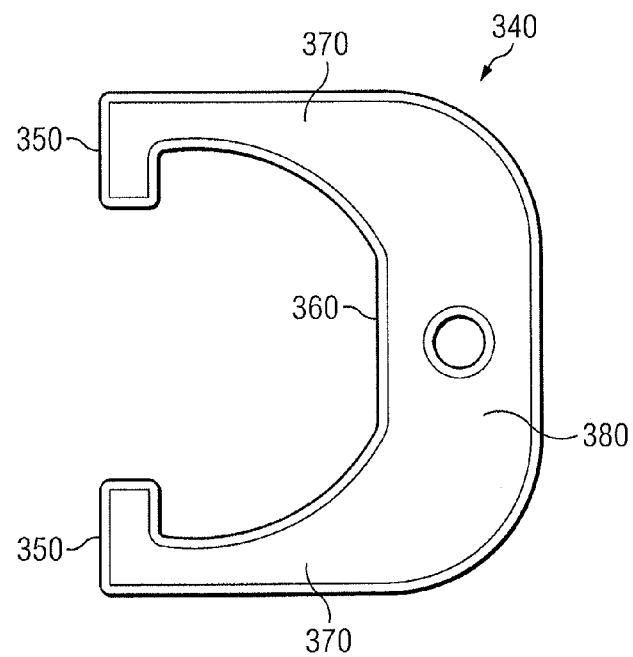
FIG. 7 illustrates a side view of an iris cup according to another exemplary embodiment of the present disclosure.
Figure 8:
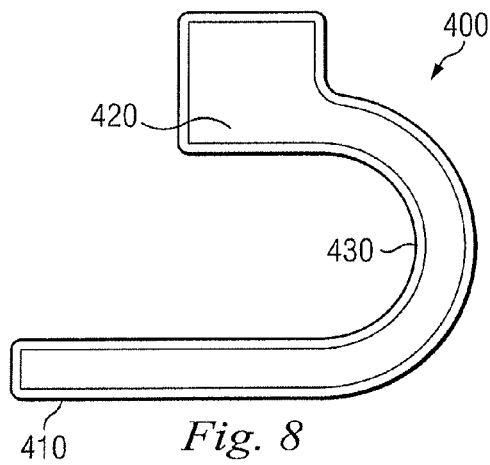
FIG. 8 illustrates a side view of an iris cup according to another exemplary embodiment of the present disclosure.

FIGS. 6-8 illustrate various examples of iris cups having different shapes and configurations. For example, FIG. 6 illustrates an iris cup 300 according to another embodiment of the present disclosure. The iris cup 300 is similar to the iris cup 120 except for the differences that can be seen by comparison of FIGS. 6 and 3 or that are noted herein. The iris cup 300 includes terminal portions 310 configured to grasp and/or apply compressive force to the iris tissue. In addition, the iris cup 300 includes a contact portion 320 shaped in part by the terminal portions 310 into a partially closed D-shape.

FIG. 7 illustrates a side view of an iris cup 340 according to another embodiment of the present disclosure. The iris cup 340 is similar to the iris cup 120 except for the differences that can be seen by comparison of FIGS. 7 and 3 or that are noted herein. The iris cup 340 includes terminal portions 350 configured to grasp and/or apply compressive force to the iris tissue. In addition, the iris cup 340 includes elongated and lengthened flanges 370 that cooperate with the terminal portions 350 to shape a contact portion into a partially closed, enlarged D-shape. The iris cup 340 also includes a central portion 380 that is enlarged, giving the iris cup 340 a larger cross-sectional profile than, for example, the iris cup 120.

FIG. 8 illustrates a side view of an iris cup 400 according to yet another embodiment of the present disclosure. The iris cup 400 is similar to the iris cup 120 except for the differences that can be seen by comparison of FIGS. 8 and 3 or that are noted herein. Similar to the iris cup 260, the iris cup 400 includes an asymmetrical cross-sectional profile wherein a posterior flange 410 is longer than an anterior flange 420. Thus, the anterior flange 420 and the posterior flange 410 are shaped and configured to engage anterior and posterior aspects of the iris, respectively, to different extents. In addition, the iris cup 400 includes a U-shaped contact surface 430 that is deeper (and may therefore provide more contact surface area) than the contact surface 210 of the iris cup 120 shown in FIG. 3.

With reference back to FIG. 1, the iris cups 120 and the iris cups 125 are substantially similar except that each iris cup 125 includes a tab 128, which comprises a ridge or rim extending into the central opening 115 that provides the user with a gripping surface for the pupil expander 100. The tab 128 allows the user to manipulate (i.e., position, reposition, remove, and/or otherwise move) the pupil expander during an ophthalmic procedure without having to contact the iris. In the pictured embodiment, the tab includes an instrument engaging feature 450 in the form of a perforation that is sized to receive an appropriate positioning tool. In other embodiments, the tab 128 may include any of a variety of instrument engaging features, including, by way of non-limiting example, grooves, protrusions, loops, and/or hooks. In alternate embodiments, the tab 128 may be positioned on the support member 110 within the recess 130. The tabs 128, by providing separate contact surfaces, may also function to protect the pupil expander 100 from damage while the pupil expander 100 is securely contained within packaging. In some embodiments, the iris cups 120 themselves include instrument engaging features that are substantially similar to the instrument engagement feature 450. For example, in some embodiments, the iris cups 120 may include instrument engaging features on the central portions 180 (shown in FIG. 2).

The pupil expander 100 may be shaped and configured to be transparent enough to provide for visualization through the support member 110 and the iris cups 120 to observe, by way of non-limiting example, underlying tissue, vessels, air bubbles, and/or bleeding. In alternate embodiments, the support member 110 and/or the iris cups 120 may be semi-transparent or opaque so as to be clearly visible during ophthalmic procedures.

Figure 9A:
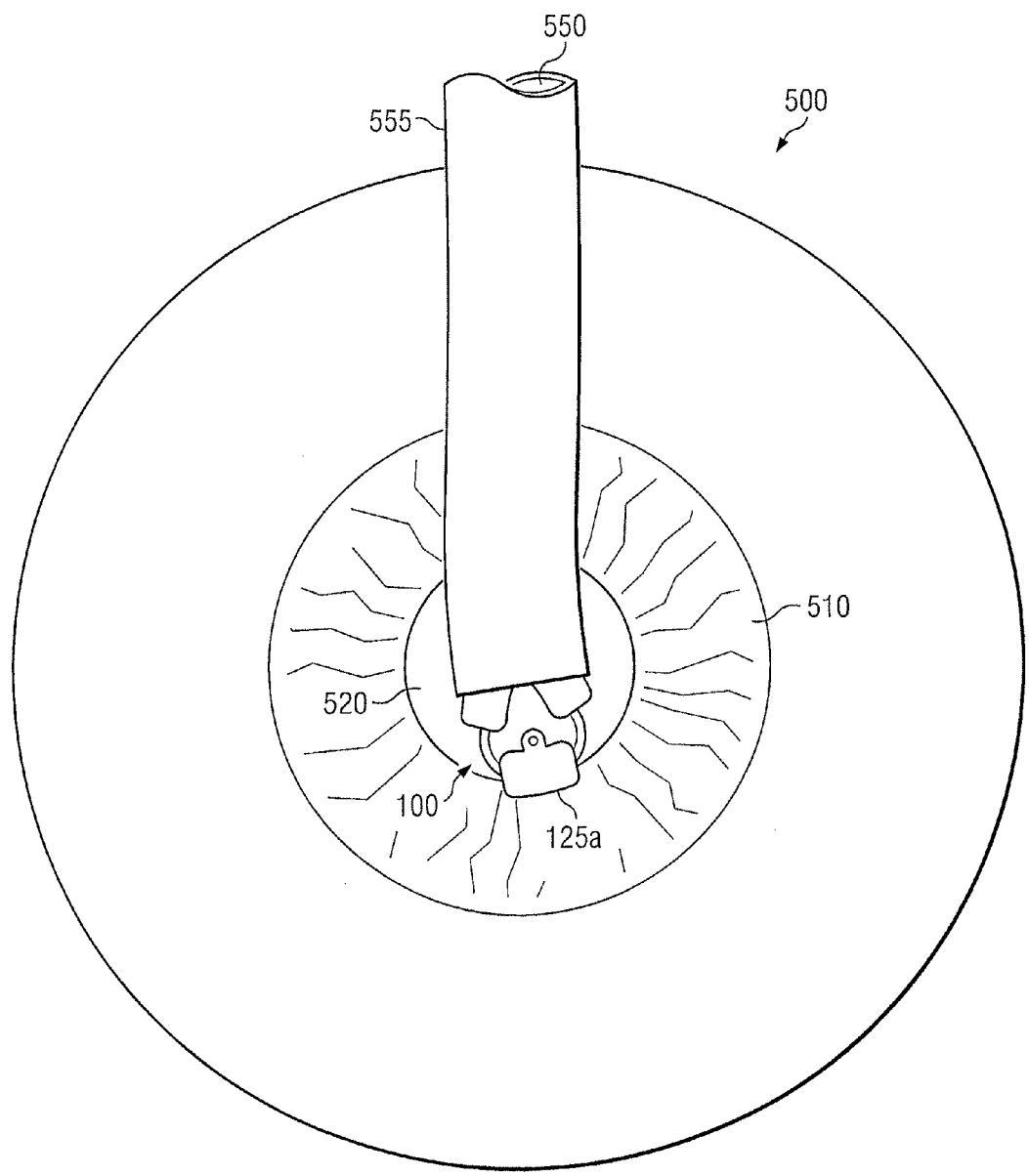
FIGS. 9a and 9b illustrate top plan views of the pupil expander shown in FIG. 1 being inserted into an eye according to one exemplary embodiment of the present disclosure.
Figure 9B:
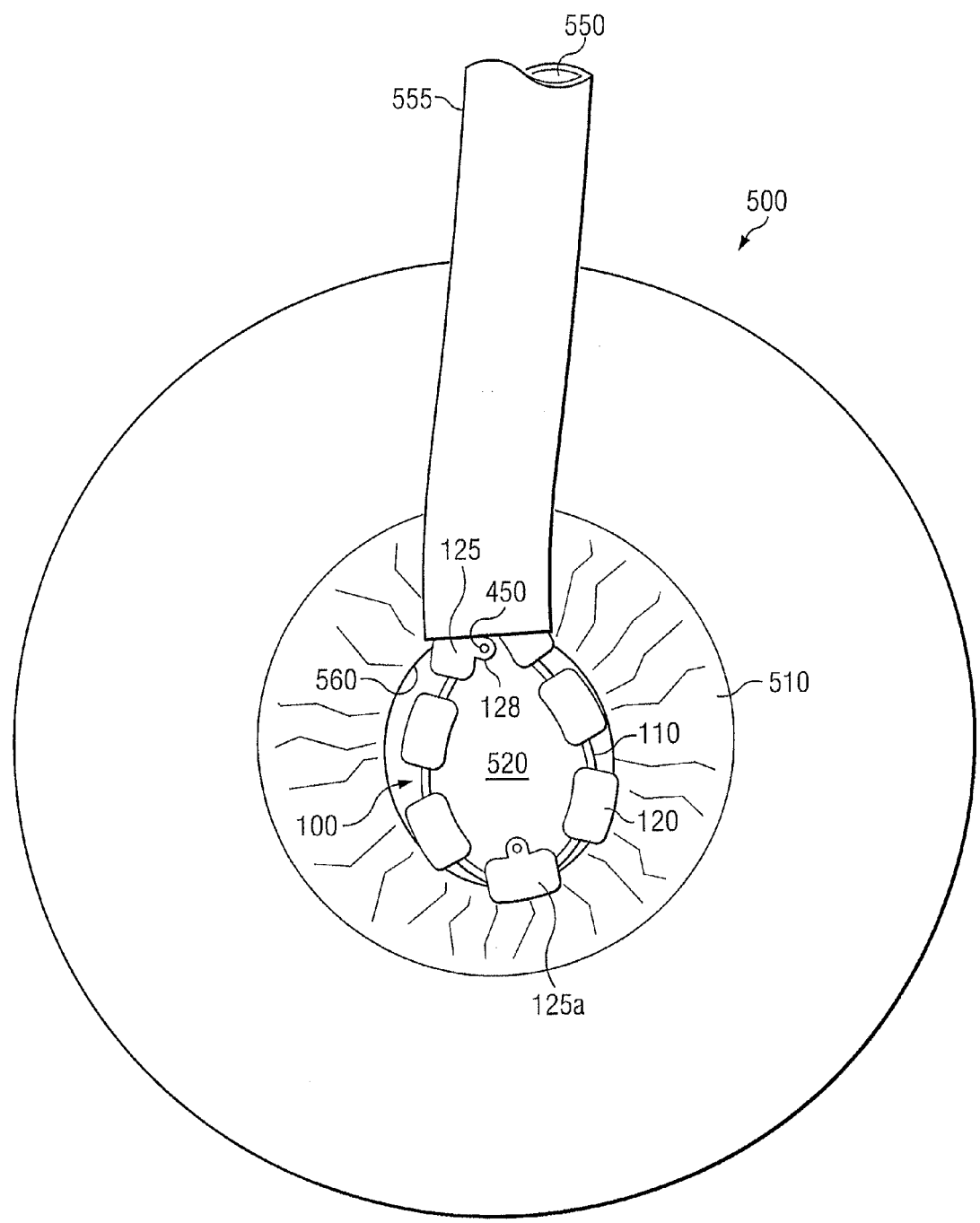
Figure 10:
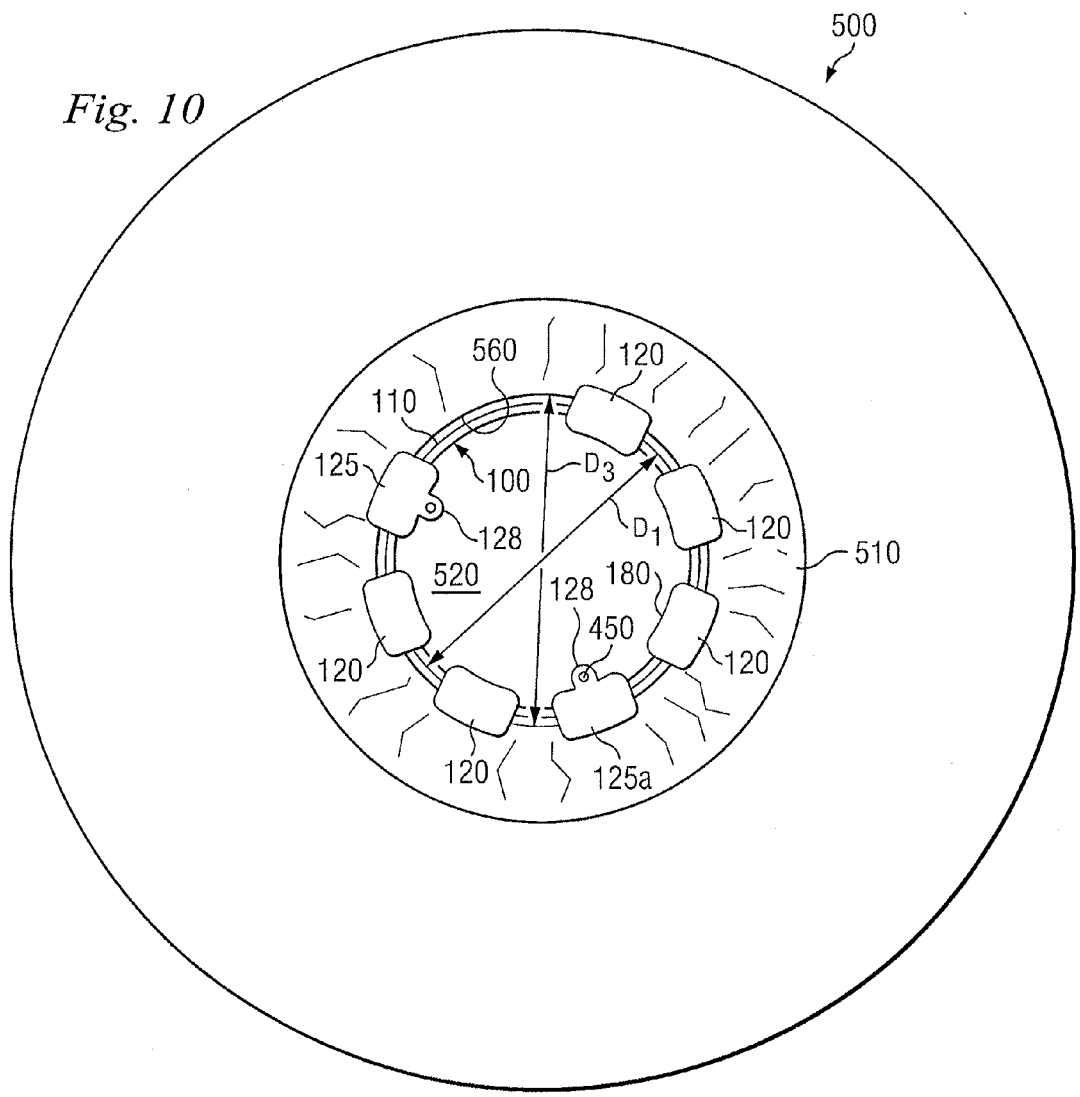
FIG. 10 illustrates a top plan view of the pupil expander shown in FIG. 1 positioned within an eye according to one embodiment of the present disclosure.
Figure 11:
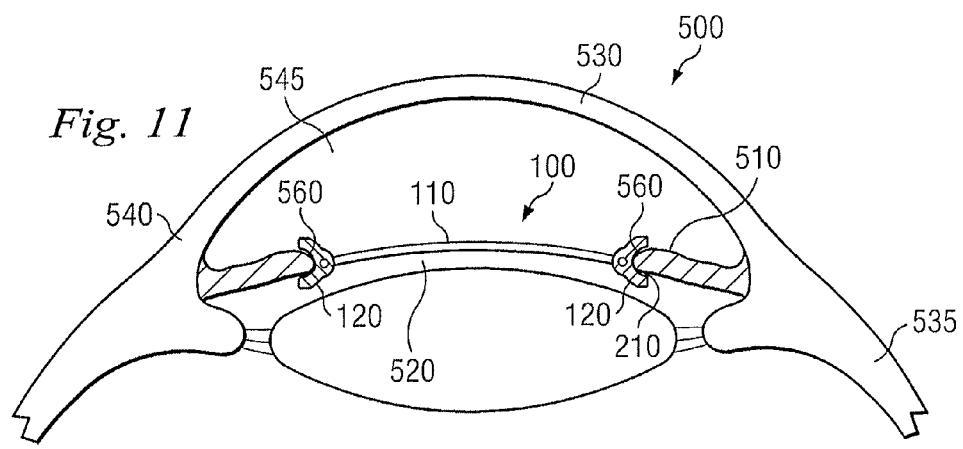
FIG. 11 illustrates a cross-sectional side view of the pupil expander shown in FIG. 1 positioned within an eye according to one embodiment of the present disclosure.

FIGS. 9*a*-11 show a method of using the pupil expander 100 in an eye 500 to stretch an iris 510 and expand a pupil 520 according to one embodiment of the present disclosure. For the sake of simplicity, only two iris cups 120 are shown in FIG. 11. With reference to FIGS. 9 and 11, after a 2-4 mm incision (not shown) is made in either a cornea 530, a sclera 535, or a limbus 540), the anterior chamber 545 is filled in a conventional manner with a viscoelastic fluid to prevent the cornea 530 from collapsing and to provide lubrication and support for the subsequent insertion of surgical instruments.

Referring to FIG. 9*a*, as the pupil expander 100 is passed into and through a lumen 550 of a delivery instrument 555, the support member 110 is in an unexpanded condition. In one exemplary method, the user may advance the pupil expander 100 from the delivery instrument 555 only to engage a distal-most (from the user) iris cup 125*a* against the iris 510. In some instances, the user may use a positioning instrument (not shown) that is inserted either through the delivery instrument 555 or through another incision (not shown) to engage the instrument engaging feature 450 of the tab 128 (labeled in FIG. 1) on the iris cup 125a to position the iris cup 125a against the iris 510. In other embodiments, the distal-most iris cup may be one of the iris cups 120.

As shown in FIG. 9b, after the iris cup 125a engages the iris 510, the user may advance the remainder of the pupil expander 100 from the delivery instrument 555 into the pupil 520. As the pupil expander 100 emerges from the delivery instrument 555 into the pupil 520, the support member 110 transitions from the unexpanded configuration into an expanded configuration having a substantially circular shape. A positioning instrument (not shown) may be utilized to manipulate the iris 510 and/or the pupil expander 100 to position the iris cups 120, 125 around an inner margin 560 of the iris 510. In some instances, the user may utilize the positioning instrument to engage the instrument engaging features 450 of the tabs 128 on the iris cups 125a, 125 to reposition the pupil expander 100.

FIGS. 10 and 11 illustrate the pupil expander 100 positioned within the eye 500 to dilate the pupil 520 in a substantially circular shape that mimics the original anatomic shape of the pupil. As shown in FIG. 10, all of the iris cups 120, 125 are positioned against the iris tissue, thereby stretching the iris 510 and expanding the pupillary diameter to a diameter D3, which slightly exceeds the external diameter D1 of the pupil expander as a result of the thickness of the central portions 180 of the iris cups 120, 125. The pupil expander 100 can maintain the pupil 520 in a dilated condition to provide a wide access or visualization field during the ophthalmic procedure.

In some embodiments, as shown in FIG. 11, the pliancy of the iris cups 120, 125 allows the contact areas 210 of the iris cups to contact and snugly surround the iris 510 at the inner iris margin 560. In some embodiments, the iris cups 120, 125 may apply a compressive force against the inner margin 560 of the iris 510, thereby stabilizing the pupil expander 100 against the iris tissue.

As illustrated in FIG. 11, the pupil expander 100 is configured to provide excellent self-retention against the eye, thereby allowing hands-free and instrument-free use of the pupil expander 100 during an ophthalmic procedure. In other words, separate means for holding the pupil expander in place within the pupil 520 are not required. The self-retaining nature of the pupil expander 100, provided by the shapes and contours of the iris cups 120, 125, eliminates the need for suturing or holding of the pupil expander 100 during use that is often required by prior art ophthalmic pupil expanding devices.

When the procedures requiring dilation are finished, the reverse of the insertion procedure depicted in FIGS. 9a and 9b is carried out. For example, in some instances, the user may use a positioning instrument to grasp the pupil expander 100 to engage the instrument engaging feature 450 of at least one of the tabs 128 to retract the pupil expander 100 into a cannula (not shown) inserted within the eye 500. The cannula may be substantially similar to the delivery instrument 555. As the pupil expander 100 is retracted into the cannula, the pupil expander 100 transitions from an expanded condition to an unexpanded condition. After retracting the entire pupil expander 100 into the cannula, the cannula, carrying the pupil expander 100 in an unexpanded condition, may be withdrawn from the eye 500.

Figure 12:
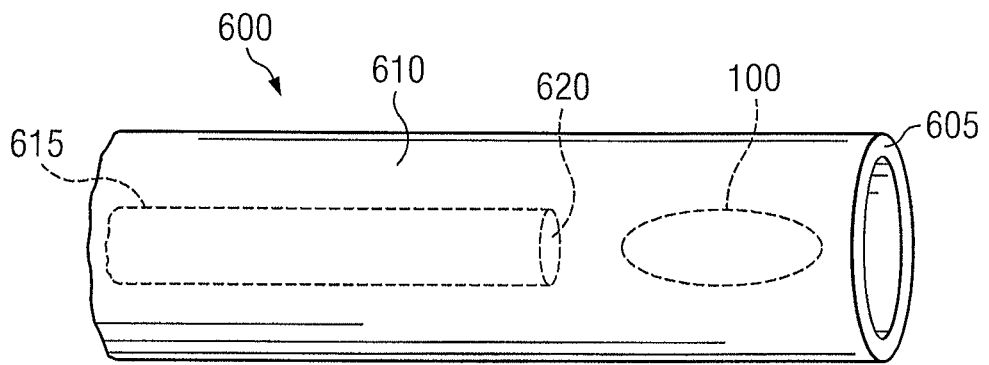
FIG. 12 illustrates a schematic view of an exemplary pupil expander delivery instrument including an exemplary plunger tip according to one embodiment of the present disclosure.

FIG. 12 illustrates a schematic view of an exemplary delivery/extraction instrument 600 for inserting and/or removing the pupil expander according to one embodiment of the present disclosure. As shown in FIG. 12, the delivery/extraction instrument 600 includes a distal end 605 in communication with a lumen 610. The delivery/extraction instrument 600 includes an insertion rod or plunger 615 longitudinally disposed within the lumen 610. The pupil expander 100 is positioned distal to a plunger tip 620 within the lumen 610 in an unexpanded condition. In some embodiments, the delivery/extraction instrument 600 is configured so that when the plunger 615 is translated towards the distal end 605 of the delivery/extraction instrument 600, the plunger tip 620 displaces the pupil expander 100 from the lumen 610, through the distal end 605, and into an eye. In some embodiments, as the pupil expander 100 emerges from the distal end 605, the pupil expander transitions from an unexpanded condition to a more expanded condition in the manner described previously.

Figure 13A:
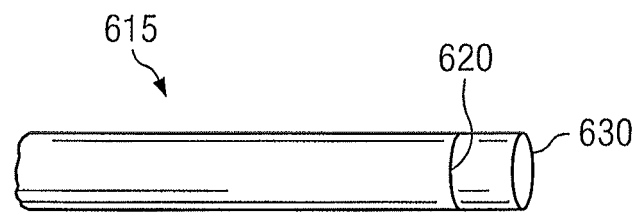
FIG. 13a illustrates a schematic view of the exemplary plunger tip shown in FIG. 12.

In the embodiment shown in FIG. 13a, the plunger 615 includes a connector 630 positioned adjacent the plunger tip 620. The connector 630 is shaped and configured to engage the pupil expander 100. The connector 630 can comprise any of a variety of shapes, including, by way of non-limiting example, a hook, a loop, a protrusion, a rod, a spiral, a tab, and a peg. In some embodiments, the connector 630 is shaped and configured to engage the instrument engaging feature 450 of the tab 128 (labeled on FIG. 1) of the pupil expander 100. In some embodiments, the instrument engaging feature 450 and the connector 630 are shaped and configured as a mating pair of selectively detachable fasteners. In other embodiments, the plunger does not include a connector.

In some embodiments, the connector 630 is fixedly attached to the plunger 615. In other embodiments, the connector 630 is selectively detachable from the plunger 615, and may be utilized during only a portion of the pupil expansion procedure. The connector 630 may be coupled to the plunger 615 by any of a variety of fastening mechanisms, including, by way of non-limiting example, using one or more of an adhesive, a threaded engagement, a snap-fit engagement, a frictional engagement, over-molding, heat-shrinking, heat welding, a hook and loop system, a latch system, and/or any other mechanism fixedly or selectively coupling the connector 630 to the plunger 615.

Figure 13B:
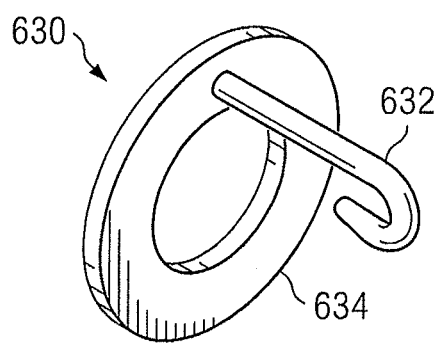
FIG. 13b illustrates a perspective view of an exemplary connector according to one embodiment of the present disclosure.

The connector 630 may be constructed from any suitable biocompatible material. In some embodiments, the connector 630 is constructed from a structurally deformable biocompatible material that can elastically or plastically deform without compromising its integrity. For example, in the embodiment depicted in FIG. 13b, the connector 630 includes a hook 632 extending from an expandable collet 634 that can selectively attach to the plunger 615. Such a collet may stretch to surround the plunger tip 620 and relax to grip the plunger tip 620 and temporarily secure the connector 630 to the plunger 615.

In some embodiments, the connector 630 is used during the removal of the pupil expander from an eye. The connector 630 may be selectively coupled to the plunger 615 before insertion (or re-insertion) of the pupil expander delivery/extraction instrument 600 into the eye (i.e., before the reverse of the insertion procedure depicted in FIGS. 9a and 9b is carried out). The delivery/extraction instrument 600 may be positioned within an eye in a substantially similar fashion as the delivery instrument 555 is positioned in FIGS. 9a and 9b. For example, in some instances, the user may use the connector 630 to grasp the pupil expander 100 by engaging the instrument engaging feature 450 of at least one of the tabs 128 before retracting the pupil expander 100 into the lumen 610 of the delivery/extraction instrument 600. After power-actuated extraction of the entire pupil expander 100 from the eye, the delivery/extraction instrument 600, carrying the pupil expander 100 in an unexpanded condition in the lumen 610, may be withdrawn from the eye.

FIGS. 14 and 15 illustrate an exemplary pupil expander delivery/extraction instrument 650 according to one embodiment of the present disclosure. In some instances, aspects of the pupil expander delivery/extraction instrument include features disclosed in U.S. patent application Ser. No. 12/249,996, entitled "Automated Intraocular Lens Injector Device," filed on Oct. 13, 2008, and U.S. patent application Ser. No. 12/763,322, entitled "Modular Intraocular Lens Injector Device," filed on Apr. 20, 2010, which are herein incorporated by reference in their entirety.

In the pictured embodiment, the delivery/extraction instrument 650 includes a cable assembly 655, a housing 660, a distal portion 663, and a distal end 665. The cable assembly 655 carries power and/or control signals from a separate user console (not shown). The delivery/extraction instrument 650 includes a plunger 667 that is longitudinally disposed within a lumen 669 of the housing 660. The plunger 667 is configured to longitudinally translate away from and towards the distal end 665. The delivery/extraction instrument 650 also comprises a cartridge mount 670 on the distal portion 665, which holds a removably mounted insertion cartridge 675.

The insertion cartridge 675 is shaped and configured to accommodate a pupil expander 100. In some embodiments, the insertion cartridge 675 includes an identifier that allows the injection apparatus 650 to recognize the contents of the insertion cartridge 675. The identification mechanism may comprise any of a variety of identification mechanisms, including without limitation a radio-frequency identifier tag, an electronic product code, and a bar code. For example, the identifier can inform the injection apparatus whether the insertion cartridge carries a pupil expander or a different ocular device, such as, by way of non-limiting example, an intraocular lens. In some instances, the identifier may inform the delivery/extraction instrument what particular type or size of pupil expander is carried in the insertion cartridge. Such identifying information may allow the delivery/extraction instrument to appropriately tailor its insertion and removal procedures.

FIG. 16 illustrates a partially cut-away perspective view of an exemplary actuating mechanism 680 of the pupil expander delivery/extraction instrument 650 shown in FIG. 14. In addition to the plunger 667, the actuating mechanism 680 includes an actuator 685 configured for longitudinal translation inside a tubular coupler 690 and an electric drive system 695. In some embodiments, the electric drive system 695 includes an electric motor. The actuating mechanism 680 is configured to linearly translate the plunger 667 along a longitudinal axis LA of the housing 660. The actuating mechanism 680 enables power-actuated insertion of the pupil expander 100.

In some embodiments, the actuating mechanism 680 also enables power-actuated extraction of the pupil expander 100.

For example, returning to FIGS. 14 and 15, as the plunger 667 is translated forward through the insertion cartridge 675, the pupil expander 100 is displaced toward the distal end 665. As the pupil expander 100 exits the delivery/extraction instrument 650 through the distal end 665, the pupil expander 100 transitions from an unexpanded condition to an expanded condition.

When the procedures requiring dilation are completed, the delivery/extraction instrument 650 may be used to extract or draw the pupil expander 100 from the eye. The actuating mechanism 680 enables the plunger 667 to translate backward through the insertion cartridge 675, thereby retracting the pupil expander 100 from the eye into the lumen 610. As the plunger 667 moves backward, the pupil expander 100 is pulled longitudinally through the lumen 610 away from the distal end 665. As the pupil expander 100 is retracted into the lumen 610, the pupil expander 100 transitions from an expanded condition to an unexpanded condition. In some embodiments, the automated mechanism of extraction of the delivery/extraction instrument 650 operates in a reverse but similar fashion to the automated mechanism of insertion described in U.S. patent application Ser. No. 12/249,996 and U.S. patent application Ser. No. 12/763,322, which were incorporated by reference in their entirety above.

After power-actuated extraction of the entire pupil expander 100 from the eye, the delivery/extraction instrument 650, carrying the pupil expander 100 in an unexpanded condition in the lumen 610, may be manually withdrawn from the eye.

The various pupil expander embodiments of the present disclosure may be configured as single-use pupil expanders that are intended to be disposable after a single use, thereby allowing for a new pupil expander for each new patient. As such, the pupil expander may be pre-sterilized before shipping to an end-user and ready for use upon receipt by the end-user. After a single use, the pupil expander may be discarded. Single-use pupil expanders ensure a sterile pupil expander for each patient without the need for sterilization by the end-user (i.e., the surgeon), thereby increasing the efficiency and safety of the ophthalmic procedure. Moreover, configuration as a single-use pupil expander allows the surgical pupil expander to be manufactured at lower cost because the disposable lens can be constructed of a relatively inexpensive biocompatible material.

The various pupil expander embodiments described herein can utilize a shape memory ring with iris cups to dilate a pupil and maintain the pupil in a dilated condition during an ophthalmic surgery or procedure. The pupil expanders described herein can assume an unexpanded condition to facilitate atraumatic insertion into and removal from an eye through a primary incision, and can assume a predetermined, expanded condition within the eye. Moreover, the various pupil expander embodiments described herein can stabilize and self-retain their position on an eye and move with the eye as necessary during a surgical or diagnostic procedure. Although the various pupil expander embodiments described herein may be used without the aid of a positioning instrument, in some embodiments, the pupil expander embodiments may be used in conjunction with a positioning instrument to provide increased control and/or maneuverability of the pupil expander in the eye.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A pupil expander system comprising:
   a support member sized to expand a pupil, the support member having a generally circumferential length and a width;
   a plurality of iris cups coupled to and spaced about the generally circumferential length of the support member, each iris cup having a recess shaped and sized to receive an inner margin of an iris, the recess located between an inner surface of a first flange and an inner surface of a second flange of each iris cup, the first and second flanges extending generally radially from the support member, and a distance between an outer surface of the first flange and an outer surface of the second flange defining a height of each iris cup; and a delivery and extraction instrument comprising a housing, a plunger longitudinally disposed within a lumen of the housing, an actuator for moving the plunger in a forward and reverse direction, and a cartridge configured to hold the pupil expander, the plunger moving through the cartridge in a forward direction to deliver the pupil expander into the eye, the plunger moving through the cartridge in a reverse direction to extract the pupil expander from the eye.

2. The pupil expander system of claim 1, wherein the support member is pliable between an expanded condition and an unexpanded condition, the expanded condition having a predetermined shape configuration and being sized to dilate the pupil.

3. The pupil expander system of claim 2, wherein the predetermined shape configuration is selected from a group consisting of an annular, closed, generally circular shape, an annular, open, generally circular shape, and an annular, polygonal shape.

4. The pupil expander system of claim 2, wherein the support member is composed of a material having shape memory.

5. The pupil expander system of claim 1, wherein the plurality of iris cups are formed of a first material and the support members is formed of a second material different than the first material.

6. The pupil expander system of claim 1, wherein the plurality of iris cups are disposed symmetrically around the support member.

7. The pupil expander system of claim 1, wherein the plurality of iris cups have a longitudinal length configured to support the iris and sized greater than 0.50 mm.

8. The pupil expander system of claim 1, wherein the plurality of iris cups include iris cups of varying sizes and shapes.

9. The pupil expander system of claim 1, wherein the plurality of iris cups includes a first iris cup and a second iris cup spaced around the support member to create a recess between the first iris cup and the second iris cup that is sized to allow passage of a cannula through the recess.

10. The pupil expander system of claim 1, wherein the plurality of iris cups have a contact surface having a curvature substantially corresponding to the curvature of the inner margin of the iris.

11. The pupil expander system of claim 10, wherein the contact surface is shaped as a concave recess sized to seat a portion of the inner margin of the iris.

12. The pupil expander system of claim 11, wherein the contact surface is shaped as a U-shape sized to seat a portion of the inner margin of the iris.

13. The pupil expander system of claim 1, wherein the plurality of iris cups are configured to conform around the inner margin of the iris.

14. The pupil expander system of claim 1, wherein at least one iris cup of the plurality of iris cups includes a tab having an instrument engagement feature.

15. The pupil expander system of claim 14, wherein the instrument engagement feature comprises a perforation.

16. The pupil expander system of claim 1, wherein at least one iris cup of the plurality of iris cups includes an instrument engagement feature.

17. The pupil expander system of claim 1, wherein at least one of the plurality of iris cups is coated with polytetrafluoroethylene.

18. The pupil expander system of claim 1, wherein one of the first flange and the second flange of at least one iris cup of the plurality of iris cups is sized and shaped differently than the other.

19. The pupil expander system of claim 1, further comprising an anterior terminal portion attached to the first flange and a posterior terminal portion attached to the second flange of at least one iris cup of the plurality of iris cups, wherein the contact surface is shaped as a concave, open D-shape sized to seat a portion of the inner margin of the iris.

* * * * *